United States Patent
Schroeder (10) Patent No.: US 7,067,046 B2
(45) Date of Patent: *Jun. 27, 2006

(54) SYSTEM FOR RAPID CHEMICAL ACTIVATION IN HIGH-THROUGHPUT ELECTROPHYSIOLOGICAL MEASUREMENTS

(75) Inventor: Kirk S. Schroeder, Ann Arbor, MI (US)

(73) Assignee: Essen Instruments, Inc., Ann Arbor, MI (US)

( * ) Notice: Subject to any disclaimer, the term of this patent is extended or adjusted under 35 U.S.C. 154(b) by 93 days.

This patent is subject to a terminal disclaimer.

(21) Appl. No.: 09/862,056

(22) Filed: May 21, 2001

(65) Prior Publication Data

US 2002/0014408 A1 Feb. 7, 2002

Related U.S. Application Data (63) Continuation-in-part of application No. 09/631,909, filed on Aug. 4, 2000, now Pat. No. 6,488,829.

(51) Int. Cl.
*G01N 33/487* (2006.01)
*C12M 1/34* (2006.01)

(52) U.S. Cl. ............... 204/403.01; 435/287.1; 435/292.1

(58) Field of Classification Search ......... 204/403.01; 435/287.1, 288.5, 292.1, 173.1, 173.5, 173.7; 422/63, 65

See application file for complete search history.

(56) References Cited

U.S. PATENT DOCUMENTS

| | | | |
|---|---|---|---|
| 3,856,633 A | 12/1974 | Fletcher, III | |
| 4,055,799 A | 10/1977 | Coster et al. | |

(Continued)

FOREIGN PATENT DOCUMENTS

| | | |
|---|---|---|
| AU | 75770/91 | 2/1995 |

(Continued)

OTHER PUBLICATIONS

Friedrich et al, Biophysical Journal, 73, 1997, pp. 186-194.*

(Continued)

*Primary Examiner*—Kaj K. Olsen
(74) *Attorney, Agent, or Firm*—Dorsey & Whitney LLP (57) ABSTRACT

An ultraviolet light source is added to a high-throughput electrophysiogical measurement system to allow for rapid chemical stimulation via caged compound release to a plurality of measurement samples. The integrated electrophysiogical measurement system includes a computer-controlled data collection system, an integrated electronics head for making parallel electrical measurements, and an integrated fluidics head used in part to transfer test compounds into the measurement process. This light source, and associated light coupling to a plurality of test samples, is used in conjunction with the system to make effectuate high-throughput electrical measurements with respect to fast-acting, chemically-activated electrophysiological events. The UV-source modification allows for rapid stimulation and measurement of multiple fast ligand-gated ion channel events in parallel.

40 Claims, 2 Drawing Sheets

U.S. PATENT DOCUMENTS

| | | |
|---|---|---|
| 4,062,750 A | 12/1977 | Butler |
| 4,071,315 A | 1/1978 | Chateau |
| 4,128,456 A | 12/1978 | Lee et al. |
| 4,225,410 A | 9/1980 | Pace |
| 4,231,660 A | 11/1980 | Remy et al. |
| 4,441,507 A | 4/1984 | Steffin |
| 4,456,522 A | 6/1984 | Blackburn |
| 4,490,216 A | 12/1984 | McConnell |
| 4,510,442 A | 4/1985 | Neher |
| 4,661,321 A | 4/1987 | Byrd et al. |
| 4,661,451 A | 4/1987 | Hansen |
| 4,803,154 A | 2/1989 | Uo et al. |
| 4,894,343 A | 1/1990 | Tanaka et al. |
| 4,911,806 A | 3/1990 | Hofmann |
| 4,912,060 A | 3/1990 | Fein |
| 4,952,518 A | 8/1990 | Johnson et al. |
| 5,009,846 A | 4/1991 | Gavet et al. |
| 5,041,266 A | 8/1991 | Fox |
| 5,055,263 A | 10/1991 | Meltzer |
| 5,111,221 A | 5/1992 | Fare et al. |
| 5,164,319 A | 11/1992 | Hafeman et al. |
| 5,169,600 A | 12/1992 | Ishizaka et al. |
| 5,187,096 A | 2/1993 | Giaever et al. |
| 5,204,239 A | 4/1993 | Gitler et al. |
| 5,225,374 A | 7/1993 | Fare et al. |
| 5,229,163 A | 7/1993 | Fox |
| 5,234,566 A | 8/1993 | Osman et al. |
| 5,262,128 A | 11/1993 | Leighton et al. |
| 5,310,469 A | 5/1994 | Cunningham et al. |
| 5,378,342 A | 1/1995 | Ikematsu et al. |
| 5,393,401 A | 2/1995 | Knoll |
| 5,443,955 A | 8/1995 | Cornell et al. |
| 5,446,186 A | 8/1995 | Ellis-Davies et al. |
| 5,506,141 A | 4/1996 | Weinreb et al. |
| 5,508,200 A | 4/1996 | Tiffany et al. |
| 5,510,628 A | 4/1996 | Georger, Jr. et al. |
| 5,512,489 A | 4/1996 | Girault et al. |
| 5,532,128 A | 7/1996 | Eggers et al. |
| 5,563,067 A | 10/1996 | Sugihara et al. |
| 5,605,662 A | 2/1997 | Heller et al. |
| 5,632,957 A | 5/1997 | Heller et al. |
| 5,750,015 A | 5/1998 | Soane et al. |
| 5,780,752 A | 7/1998 | Okubo et al. |
| 5,810,725 A | 9/1998 | Sugihara et al. |
| 5,858,804 A | 1/1999 | Zanzucchi et al. |
| 5,889,216 A | 3/1999 | Okubo et al. |
| 5,904,824 A | 5/1999 | Oh |
| 5,911,871 A | 6/1999 | Preiss et al. |
| 5,936,728 A | 8/1999 | Bouzid ............... 356/318 |
| 5,955,352 A | 9/1999 | Inoue et al. |
| 5,958,345 A | 9/1999 | Turner et al. |
| 5,962,081 A | 10/1999 | Öhman et al. |
| 5,981,268 A | 11/1999 | Kovacs et al. |
| 6,008,010 A | 12/1999 | Greenberger et al. |
| 6,015,714 A | 1/2000 | Baldarelli et al. |
| 6,027,695 A | 2/2000 | Oldenburg et al. |
| 6,032,062 A | 2/2000 | Nisch |
| 6,033,916 A | 3/2000 | Sieben et al. |
| 6,043,037 A | 3/2000 | Lucas |
| 6,048,722 A | 4/2000 | Farb et al. |
| 6,056,861 A | 5/2000 | Fuhr et al. |
| 6,063,260 A | 5/2000 | Olesen et al. ............ 205/793 |
| 6,068,818 A | 5/2000 | Ackley et al. |
| 6,093,296 A | 7/2000 | Soane et al. |
| 6,099,803 A | 8/2000 | Ackley et al. |
| 6,103,479 A | 8/2000 | Taylor |
| 6,106,784 A | 8/2000 | Lund et al. |
| 6,113,768 A | 9/2000 | Fuhr et al. |
| 6,117,291 A | 9/2000 | Olesen et al. |
| 6,132,582 A | 10/2000 | King et al. |
| 6,143,496 A | 11/2000 | Brown et al. |
| 6,151,519 A | 11/2000 | Sugihara et al. |
| 6,156,181 A | 12/2000 | Parce et al. |
| 6,163,719 A | 12/2000 | Sherman |
| 6,177,000 B1 | 1/2001 | Peterson |
| 6,207,031 B1 | 3/2001 | Adourian et al. |
| 6,225,059 B1 | 5/2001 | Ackley et al. |
| 6,228,326 B1 | 5/2001 | Boxer et al. |
| 6,235,520 B1 | 5/2001 | Malin et al. |
| 6,267,872 B1 | 7/2001 | Akeson et al. |
| 6,277,629 B1 | 8/2001 | Wolf et al. |
| 6,284,113 B1 | 9/2001 | Bjornson et al. |
| 6,284,872 B1 | 9/2001 | Celeste et al. |
| 6,287,517 B1 | 9/2001 | Ackley et al. |
| 6,315,940 B1 | 11/2001 | Nisch et al. |
| 6,329,209 B1 | 12/2001 | Wagner et al. |
| 6,355,491 B1 | 3/2002 | Zhou et al. |
| 6,365,129 B1 | 4/2002 | Fogarty |
| 6,368,851 B1 | 4/2002 | Baumann et al. |
| 6,376,233 B1 | 4/2002 | Wolf et al. |
| 6,377,057 B1 | 4/2002 | Borkholder |
| 6,379,916 B1 | 4/2002 | Meyer |
| 6,448,794 B1 | 9/2002 | Cheng et al. |
| 6,461,860 B1 | 10/2002 | Mathes et al. |
| 6,470,226 B1 | 10/2002 | Olesen et al. |
| 6,475,760 B1 | 11/2002 | Baumann et al. |
| 6,475,808 B1 | 11/2002 | Wagner et al. |
| 6,488,829 B1 | 12/2002 | Schroeder et al. |
| 6,596,143 B1 | 7/2003 | Wang et al. |
| 6,602,714 B1 | 8/2003 | Tagge et al. |
| 6,613,285 B1 | 9/2003 | Carnahan |
| 6,630,835 B1 | 10/2003 | Cheng et al. |
| 6,635,470 B1 | 10/2003 | Vann |
| 6,638,743 B1 | 10/2003 | Baumann et al. |
| 6,649,357 B1 | 11/2003 | Bryan et al. |
| 6,668,230 B1 | 12/2003 | Mansky et al. |
| 6,670,115 B1 | 12/2003 | Zhang |
| 6,682,649 B1 | 1/2004 | Petersen et al. |
| 6,699,697 B1 | 3/2004 | Klemic et al. |
| 6,762,036 B1 | 7/2004 | Farb et al. |
| 2001/0005489 A1 | 6/2001 | Roach et al. |
| 2001/0005774 A1 | 6/2001 | Kato et al. |
| 2001/0045359 A1 | 11/2001 | Cheng et al. |
| 2002/0063067 A1 | 5/2002 | Bech et al. |
| 2002/0072103 A1 | 6/2002 | Matsumoto et al. |
| 2002/0074227 A1 | 6/2002 | Nisch et al. |
| 2002/0076825 A1 | 6/2002 | Cheng et al. |
| 2002/0104757 A1 | 8/2002 | Schmidt |
| 2002/0108869 A1 | 8/2002 | Savtchenko |
| 2002/0119579 A1 | 8/2002 | Wagner |
| 2002/0137121 A1 | 9/2002 | Rubinsky et al. |
| 2002/0144905 A1 | 10/2002 | Schmidt |
| 2002/0155586 A1 | 10/2002 | Cheng et al. |
| 2002/0164777 A1 | 11/2002 | Kelly et al. |
| 2002/0182627 A1 | 12/2002 | Wang et al. |
| 2002/0190732 A1 | 12/2002 | Cheng et al. |
| 2002/0195337 A1 | 12/2002 | Osipchuk et al. |
| 2003/0022268 A1 | 1/2003 | Lepple-Wienhues |
| 2003/0052002 A1 | 3/2003 | Vogel et al. |
| 2003/0059936 A1 | 3/2003 | Baumann et al. |
| 2003/0070923 A1 | 4/2003 | Schroeder et al. |
| 2003/0080314 A1 | 5/2003 | Nisch et al. |
| 2003/0098248 A1 | 5/2003 | Vogel et al. |
| 2003/0104512 A1 | 6/2003 | Freeman et al. |
| 2003/0121778 A1 | 7/2003 | Dodgson et al. |
| 2003/0129581 A1 | 7/2003 | Owen et al. |
| 2003/0132109 A1 | 7/2003 | Bullen et al. |
| 2003/0134416 A1 | 7/2003 | Yamanishi et al. |
| 2003/0138767 A1 | 7/2003 | Bullen et al. |
| 2003/0139336 A1 | 7/2003 | Norwood et al. |
| 2003/0146091 A1 | 8/2003 | Vogel et al. |
| 2003/0153067 A1 | 8/2003 | Stett et al. |
| 2003/0219884 A1 | 11/2003 | Lison et al. |
| 2004/0062685 A1 | 4/2004 | Norton et al. |

| | | |
|---|---|---|
| 2004/0251145 A1 | 12/2004 | Robertson |

FOREIGN PATENT DOCUMENTS

| | | |
|---|---|---|
| DE | 4115414 | 11/1992 |
| DE | 19605830 | 2/1997 |
| DE | 19628928 | 1/1998 |
| DE | 19646505 | 5/1998 |
| DE | 19712309 | 5/1998 |
| DE | 19815882 | 10/1999 |
| DE | 19827957 | 12/1999 |
| DE | 19936302 | 2/2001 |
| DE | 19948473 | 4/2001 |
| DE | 19961951 | 6/2001 |
| DE | 10008373 | 9/2001 |
| DE | 10022772 | 11/2001 |
| DE | 10047390 | 4/2002 |
| DE | 10061347 | 6/2002 |
| DE | 20220299 | 5/2003 |
| DE | 10218325 | 11/2003 |
| DE | 10254158 | 6/2004 |
| DE | 10320899 | 12/2004 |
| EP | 0094193 | 5/1983 |
| EP | 0299778 | 1/1989 |
| EP | 0299779 | 1/1989 |
| EP | 0162907 | 1/1992 |
| EP | 0639768 | 2/1995 |
| EP | 0960933 | 5/1999 |
| EP | 0962524 | 9/1999 |
| EP | 1035918 | 9/2000 |
| EP | 1040349 | 10/2000 |
| EP | 1178315 | 2/2002 |
| EP | 1203823 | 5/2002 |
| EP | 0689051 | 11/2002 |
| EP | 1333279 | 8/2003 |
| EP | 1418427 | 5/2004 |
| FR | 2659347 | 9/1991 |
| GB | 2360162 | 5/2001 |
| GB | 2355354 | 4/2002 |
| GB | 2 371 626 | 7/2002 |
| GB | 2401689 | 11/2004 |
| JP | 4-204211 | 7/1992 |
| JP | 4-204244 | 7/1992 |
| JP | 4-338240 | 11/1992 |
| JP | 2003-307481 | 10/2003 |
| JP | 2004301529 | 10/2004 |
| WO | WO 85/02201 | 5/1985 |
| WO | WO 89/01159 | 2/1989 |
| WO | WO 91/13977 | 9/1991 |
| WO | WO 92/21020 | 11/1992 |
| WO | WO 94/15701 | 7/1994 |
| WO | WO 94/25862 | 11/1994 |
| WO | WO 96/13721 | 5/1996 |
| WO | WO 97/17426 | 5/1997 |
| WO | WO 97/22875 | 6/1997 |
| WO | WO 97/25616 | 7/1997 |
| WO | WO 97/40104 | 10/1997 |
| WO | WO 97/46882 | 12/1997 |
| WO | WO 97/49987 | 12/1997 |
| WO | WO 98/01150 | 1/1998 |
| WO | WO 98/22819 | 5/1998 |
| WO | WO 98/47003 | 10/1998 |
| WO | WO 98/54294 | 12/1998 |
| WO | WO 98/58248 | 12/1998 |
| WO | WO 99/19729 | 4/1999 |
| WO | WO 99/28037 | 6/1999 |
| WO | WO-99/31503 * | 6/1999 |
| WO | WO 99/34202 | 7/1999 |
| WO | WO 99/39829 | 8/1999 |
| WO | WO 99/66329 | 12/1999 |
| WO | WO 00/25121 | 5/2000 |
| WO | WO 00/34776 | 6/2000 |
| WO | WO 00/71742 | 11/2000 |
| WO | WO 01/07583 | 2/2001 |
| WO | WO 01/07584 | 2/2001 |
| WO | WO 01/07585 | 2/2001 |
| WO | WO 01/25769 | 4/2001 |
| WO | WO 01/27614 | 4/2001 |
| WO | WO 01/34764 | 5/2001 |
| WO | WO 01/48474 | 7/2001 |
| WO | WO 01/48475 | 7/2001 |
| WO | WO 01/59153 | 8/2001 |
| WO | WO 01/59447 | 8/2001 |
| WO | WO 01/69241 | 9/2001 |
| WO | WO 01/71349 | 9/2001 |
| WO | WO 01/75438 | 10/2001 |
| WO | WO 01/81425 | 11/2001 |
| WO | WO 01/86290 | 11/2001 |
| WO | WO 01/94939 | 12/2001 |
| WO | WO 02/00217 | 1/2002 |
| WO | WO 02/02608 | 1/2002 |
| WO | WO 02/03058 | 1/2002 |
| WO | WO 02/04656 | 1/2002 |
| WO | WO 02/08748 | 1/2002 |
| WO | WO 02/10747 | 2/2002 |
| WO | WO 02/12896 | 2/2002 |
| WO | WO 02/16936 | 2/2002 |
| WO | WO 02/27909 | 4/2002 |
| WO | WO 02/28523 | 4/2002 |
| WO | WO 02/29402 | 4/2002 |
| WO | WO 02/31505 | 4/2002 |
| WO | WO 02/52045 | 7/2002 |
| WO | WO 02/59597 | 8/2002 |
| WO | WO 02/59598 | 8/2002 |
| WO | WO 02/59603 | 8/2002 |
| WO | WO 02/65092 | 8/2002 |
| WO | WO 02/66596 | 8/2002 |
| WO | WO 02/73159 | 9/2002 |
| WO | WO 02/74983 | 9/2002 |
| WO | WO 02/77259 | 10/2002 |
| WO | WO 02/77627 | 10/2002 |
| WO | WO 02/82046 | 10/2002 |
| WO | WO 02/095357 | 11/2002 |
| WO | WO 02/103354 | 12/2002 |
| WO | WO 03/021230 | 3/2003 |
| WO | WO 03/046216 | 6/2003 |
| WO | WO 03/047738 | 6/2003 |
| WO | WO 03/067251 | 8/2003 |
| WO | WO 03/089564 | 10/2003 |
| WO | WO 03/093494 | 11/2003 |
| WO | WO 04/011084 | 2/2004 |
| WO | WO 04/018690 | 3/2004 |
| WO | WO 04/021002 | 3/2004 |
| WO | WO 04/034052 | 4/2004 |
| WO | WO 04/038410 | 5/2004 |
| WO | WO 04/044574 | 5/2004 |
| WO | WO 04/074829 | 9/2004 |
| WO | WO 04/100229 | 11/2004 |
| WO | WO 05/007866 | 1/2005 |
| WO | WO 05/012554 | 2/2005 |

OTHER PUBLICATIONS

Parpura V., Haydon PG., "UV photolysis using a micromanipulated optical fiber to deliver UV energy directly to the sample", Abstract dated Feb. 1999 printed, from NCBI website.

T. Suga, M. Hirano, M. Takayanagi, H. Koshimoto, A. Watanabe, "Restricted photorelease of biologically active molecules near the plasma membrane", Abstracted dated Dec. 1998, printed from NCBI website.

R. J. Delay, A. E. Dubin, V. E. Dionne, "A cyclic nucleotide-dependent chloride conductance in olfactory receptor neurons", Sep. 1, 1997, Abstract printed from NCBI website.

J. A. McCray, D. R. Trentham, "Properties and uses of photoreactive caged compounds", 1989, Abstract printed from NCBI website.

H. Tanaka, R. B. Clark, W. R. Giles, "Positive chronotropic responses of rabbit sin-atrial node cells to flash photolysis of caged isoproterenol and cyclic AMP", Mar. 22, 1996, Abstracted printed from NCBI website.

*Haptotaxis and the Mechanism of Cell Motility*, Carter, Nature, pp. 256-261, Jan. 21, 1967.

*Effect of Internal Fluoride and Phosphate on Membrane Currents During Intracellular Dialysis of Nerve Cells*, Kostyuk et al., Nature, vol. 257, pp. 691-693, Oct. 23, 1975.

*Adhesion of Cells to Surfaces Coated with Polylysine*, Mazia et al., Journal of Cell Biology, vol. 66, pp. 198-200, 1975.

*The Feynman Lectures on Physics*, Feynman et al., pp. 10-1 through 10-5, © Feb. 1977.

*Role of Electrogenic Sodium Pump in Slow Synaptic Inhibition is Re-evaluated*, Kostyuk et al., Nature, vol. 267, May 5, 1977.

*Fusion of Phospholipid Vesicles with Planar Phospholipid Bilayer Membranes*, Cohen et al., J. Gen. Physiol., vol. 75, pp. 251-270, Mar. 1980.

*Improved Patch-Clamp Techniques for High-Resolution Current Recording From Cells and Cell-Free Membrane Patches*, Hamill et al., Pflügers Arch., vol. 391, pp. 85-100, 1981.

*Preparation of Large Unilamellar Vesicles*, Hub et al., FEBS Letters, vol. 140, No. 2, pp. 254-256, Apr. 1982.

*Formation and Properties of Cell-Sized Lipid Bilayer Vesicles*, Mueller et al., Biophysics Journal, vol. 44, pp. 375-381, Dec. 1983.

*Perfusion of Oocytes*, Yoshii et al., Intracellular Perfusion of Excitable Cells, pp. 77-89, 1984.

*Intracellular Perfusion of Excitable Cells*, Kostyuk et al., pp. 35-51, 1984.

*Novel Method of Cell Fusion in Field Constriction Area in Fluid Integrated Circuit*, Masuda et al., IEEE Trans. IAS, XP-002181725, pp. 1549-1553, Oct. 1987.

*A Membrane Fusion Strategy for Single-Channel Recordings of Membranes Usually Non-Accessible to Patch-Clamp Pipette Electrodes*, Criado et al., FEBS Letters, vol. 224, No. 1, pp. 172-176, Nov. 1987.

*Muscarinic Activation of Ionic Currents Measured by a New Whole-Cell Recording Method*, Horn et al., Journal of General Physiology, vol. 92, pp. 145-159, Aug. 1988.

*Controlled Outgrowth of Dissociated Neurons on Patterned Substrates*, Kleinfeld et al., The Journal of Neuroscience, vol. 8, No. 11, pp. 4098-4120, Nov. 1988.

*Single Channel Recordings of Reconstituted Ion Channel Proteins: An Improved Technique*, Keller et al., Pflügers Arch., vol. 411, pp. 94-100, 1988.

*Anti-T2 Monoclonal Antibody Immobilization on Quartz Fibers: Stability and Recognition of T2 Mycotoxin*, Williamson et al., Analytical Letters, vol. 22, No. 4, pp. 803-816, 1989.

*Current-Voltage Relationships of a Sodium-Sensitive Potassium Channel in the Tonoplast of Chara Corallina*, Bertl, Journal of Membrane Biology, vol. 109, pp. 9-19, 1989.

*Optimizing Planar Lipid Bilayer Single-Channel Recordings for High Resolution with Rapid Voltage Steps*, Wonderlin et al., Biophysics Journal, vol. 58, pp. 289-297, Aug. 1990.

*Patch Clamp of Cation Channels*, Lewis et al., Current Topics in Membranes and Transport, vol. 37, pp. 215-245, 1990.

*Reconstitution of Epithelial Ion Channels*, Bridges et al., Current Topics in Membranes and Transport, vol. 37, pp. 283-312, 1990.

*Low Access Resistance Perforated Patch Recordings Using Amphotericin B*, Rae et al., Journal of Neuroscience Methods, vol. 37, pp. 15-26, 1991.

*Receptor Screening and the Search for New Pharmaceuticals*, Hodgson, Bio-Technology, vol. 10, pp. 973-980, Sep. 1992.

*Functional Reconstitution of the Nicotinic Acetylcholine Receptor by CHAPS Dialysis Depends on the Concentrations of Salt, Lipid, and Protein*, Schürholz et al., Biochemistry, vol. 31, pp. 5067-5077, 1992.

*Patch Voltage Clamping with Low-Resistance Seals: Loose Patch Clamp*, Roberts et al., Methods in Enzymology, vol. 207, pp. 155-176, 1992.

*Insertion of Ion Channels into Planar Lipid Bilayers by Vesicle Fusion*, Labarca et al., Methods in Enzymology, vol. 207, pp. 447-463, 1992.

*Patch Clamp Techniques: An Overview*, Cahalan et al., Methods in Enzymology, vol. 207, pp. 3-14, 1992.

*Glass Technology for Patch Clamp Electrodes*, Rae et al., Methods in Enzymology, vol. 207, pp. 66-92, 1992.

*Planar Lipid Bilayers on Patch Pipettes: Bilayer Formation and Ion Channels Incorporation*, Ehrlich, Methods in Enzymology, vol. 207, pp. 463-470, 1992.

*The Axon Guide for Electrophysiology and Biophysics Laboratory Techniques*, Axon Instruments, Inc., Jun. 1993.

*Molecular Biology of the Cell*, Third Edition, Alberts et al., pp. 178-189, © 1994.

*Modeling Success and Failure of Langmuir-Blodgett Transfer of Phospholipid Bilayers to Silicon Dioxide*, Osborn et al., Biophysical Journal, vol. 68, pp. 1364-1373, Apr. 1995.

*Patterning Self-Assembled Monolayers Using Microcontact Printing: A New Technology for Biosensors?*, Mrksich et al., TBTech, vol. 13, pp. 228-235, Jun. 1995.

*Lipid Vesicle Adsorption Versus Formation of Planar Bilayers on Solid Surfaces*, Nollert et al., Biophysical Journal, vol. 69, pp. 1447-1455, Oct. 1995.

*Phenomenology and Kinetics of Lipid Bilayer Spreading on Hydrophilic Surfaces*, Rädler et al., Langmuir, vol. 11, No. 11, pp. 4539-4548, 1995.

*A Highly Stable and Selective Biosensor Using Modified Nicotinic Acetylcholine Receptor (nAChR)*, Eray et al., BioSystems, vol. 35, pp. 183-188, 1995.

*G Proteins and Regulation of Adenylate Cyclase (Nobel Lecture)*, Gilman, Angew. Chem. Int. Ed. Engl., vol. 34, pp. 1406-1419, 1995.

*Signal Transduction: Evolution of an Idea (Nobel Lecture)*, Rodbell, Angew. Chem. Int. Ed. Engl., vol. 34, pp. 1420-1428, 1995.

*Shape Change and Physical Properties of Gian Phospholipid Vesicles Prepared in the Presence of an AC Electric Field*, Mathivet et al., Biophysical Journal, vol. 70, pp. 1112-1121, Mar. 1996.

McCrone "Microscopy" from Kirk-Othmer, *Encyclopedia of Chemical Technology*, pp. 651, 658-659, 1995.

*Ion Channels from Synaptic Vesicle Membrane Fragments Reconstituted into Lipid Bilayers*, Kelly et al., Biophysical Journal, vol. 70, pp. 2593-2599, Jun. 1996.

*Controlling Cell Attachment on Contoured Surfaces with Self-Assembled Monolayers of Alkanethiolates on Gold*, Mrksich et al., Proc. Natl. Acad. Sci USA, vol. 93, pp. 10775-10778, Oct. 1996.

*Preparation of Giant Liposomes on Physiological Conditions and Their Characterization Under an Optical Microscope*, Akashi et al., *Biophysical Journal*, vol. 71, pp. 3242-3250, Dec. 1996.
*Preparation of Giant Myelin Vesicles and Proteoliposomes to Register Ionic Channels*, Regueiro et al., *Journal of Neurochemistry*, vol. 67, No. 5, pp. 2146-2154, 1996.
*Critical Dependence of the Solubilization of Lipid Vesicles by the Detergent CHAPS on the Lipid Composition. Functional Reconstitution of the Nicotinic Acetylcholine Receptor Into Preformed Vesicles Above the Critical Micellization Concentration*, Schürholz, *Biophysical Chemistry*, vol. 58, pp. 87-96, 1996.
*A Novel Chloride Channel in Vicia faba Guard CellVacuoles Activated by the Serine/Threonine Kinase, CDPK*, Pei et al., *EMBO Journal*, vol. 15, No. 23, pp. 6564-6574, 1996.
*Investigating Channel Activity*, Aidley et al., *Ion Channels: Molecules in Action*, pp. 33-57, 1996.
*Single Binding Versus Single Channel Recordings: A New Approach to Study Ionotropic Receptors*, Edelstein et al., *Biochemistry*, vol. 36, No. 45, pp. 13755-17650, 1997.
*Nystatin/Ergosterol Method for Reconstituting Ion Channels into Planar Lipid Bilayers*, Woodbury, *Methods in Enzymology*, vol. 294, pp. 319-350, 1999.
*Isolation of Transport Vesicles that Deliver Ion Channels to the Cell Surface*, Sattsangi et al., *Methods in Enzymology*, vol. 294, pp. 339-350 (abstract only included), 1999.
*New UC Berkeley "Bionic Chip" Features Living Biological Cell Successfully Merged With Electronic Circuitry*, University of California Berkeley, Press Release, Feb. 25, 2000.
*Researchers Make 'Bionic Chip,'* Edwards, Associated Press, Feb. 25, 2000.
*A Chip-Based Biosensor for the Functional Analysis of Single Ion Channels*, Schmidt et al., Angew. Chem. Int. Ed. 2000, vol. 39, No. 17, pp. 3137-3140, 2000.
*Osmotically Evoked Shrinking of Guard-Cell Protoplasts Causes Vesicular Retrieval of Plasma Membrane into the Cytoplasm*, Kubitscheck et al., *Planta*, vol. 210, pp. 423-431, 2000.
Hungary Patent Document No. HU 200000996, dated Nov. 28, 2001.
*The Lipid Bilayer Concept and its Experimental Realization: From Soap Bubbles, Kitchen Sink, to Bilayer Lipid Membranes*, Tien et al., *Journal of Membrane Science*, vol. 189, pp. 83-117, 2001.
*NEURON Programming Tutorial #1*, Martin, Internet pp. 1-7, Mar. 3, 2002.
*Introduction to Voltage Clamp and Current Clamp*, Purves, Internet pp. 1-2, Mar. 3, 2002.
*Microfluidics-Based lab-on-a-chip Systems*, Weigl, *IVDT*, pp. 1-6, internet reprint Apr. 11, 2002.
*Patch Clamping Directly Measures Ionic Current*, Sophion Bioscience, Internet pp. 1-2, May 1, 2002.
*Patch Clamp Technique*, Nanion Products, Internet pp. 15, May 1, 2002.
*Patch Clamp on a Chip*, Sigworth et al., *Biophysical Journal*, vol. 82, pp. 2831-2832, Jun. 2002.
*A Microfabricated Chip for the Study of Cell Electroporation*, Huang et al., pp. 1-4, undated.
*Intracellular Perfusion of Helix Giant Neurons*, Kryshtal et al., *Neirofiziologiya*, vol. 7, No. 3, pp. 327-329 (reprinted in English as pp. 258-259), May-Jun. 1975.
*Current Fluctuations, Associated with the Activation of Calcium Channel Mechanism in the Membrane of Nerve Cells*, Kristhal et al., *USSR Academy of Science Report*, vol. 231, No. 5, 1976.
*Asymmetrical Displacement Currents in Nerve Cell Membrane and Effect of Internal Fluoride*, Kostyuk et al., *Nature*, vol. 267, pp. 70-72, May 5, 1977.
*Separation of Sodium and Calcium Currents in the Somatic Membrane of Mollusc Neurones*, Kostyuk et al., *J. Physiol.*, vol. 270, pp. 545-568, 1977.
*Properties of Internally Perfused, Voltage-Clamped, Isolated Nerve Cell Bodies*, Lee et al., *Journal of General Physiology*, vol. 71, pp. 489-507, 1978.
*The Extracellular Patch Clamp: A Method for Resolving Currents Through Individual Open Channels in Biological Membranes*, Neher et al., *Pflugers Arch.*, vol. 375, pp. 219-228, 1978.
*Ionic Currents in the Neuroblastoma Cell Membrane*, Kostyuk et al., *Neuroscience*, vol. 3, pp. 327-332, 1978.
*Effects of Internal Free Calcium Upon the Sodium and Calcium Channels in the Tunicate Egg Analysed by the Internal Perfusion Technique*, Takahashi et al., vol. 279, pp. 519-549, 1978.
*Single Acetylcholine-Activated Channels Show Burst-Kinetics in Presence of Desensitizing Concentrations of Agonist*, Sakmann et al., *Nature*, vol. 286, pp. 71-73, Jul. 3, 1980.
*Single Na+ Channel Currents Observed in Cultured Rat Muscle Cells*, Sigworth et al., *Nature*, vol. 287, pp. 447-449, Oct. 2, 1980.
*A Receptor for Protons in the Nerve Cell Membrane*, Krishtal et al., *Neuroscience*, vol. 5, pp. 2325-2327, 1980.
*Fluctuations in the Microsecond Time Range of the Current Through Single Acetylcholine Receptor Ion Channels*, Colquhoun et al., *Nature*, vol. 294, pp. 464-466, Dec. 3, 1981.
*Intracellular Perfusion*, Kostyuk et al., *Journal of Neuroscience Methods*, vol. 4, pp. 201-210, 1981.
*Receptor for Protons in the Membrane of Sensory Neurons*, Krishtal et al., *Brain Research*, vol. 214, pp. 150-154, 1981.
*A 'Receptor' for Protons in Small Neurons of Trigeminal Ganglia: Possible Role in Nociception*, Krishtal et al., *Neuroscience Letters*, vol. 24, pp. 243-246, 1981.
*Intracellular Perfusion*, Kostyuk, *Ann. Rev. Neurosci.*, vol. 5, pp. 102-120, 1982.
*Science and Technology of Patch-Recording Electrodes*, Corey et al., *Single-Channel Recording*, pp. 53-68, 1983.
*Perfusion of Isolated Neurons Fixed in Plastic Film*, Kostyuk et al., *Intracellular Perfusion of Excitable Cells*, pp. 35-51, 1984.
*Electrical Measurements on Perfused Cells*, Osipchuk et al., *Intracellular Perfusion of Excitable Cells*, pp. 103-129, 1984.
*The Patch Clamp is More Useful Than Anyone had Expected*, Sigworth, *Federation Proceedings*, vol. 45, No. 12, pp. 2673-2677, Nov. 1986.
*Quantitative Video Microscopy of Patch Clamped Membranes Stress, Strain, Capacitance, and Stretch Channel Activation*, Sokabe et al., *Biophysical Journal*, vol. 59, pp. 722-728, Mar. 1991.
*Perfusion of Nerve Cells and Separation of Sodium and Calcium Currents*, Kostyuk, *Cellular Neurobiology: A Practical Approach*, pp. 121-135, 1991.
*The Patch Clamp Technique*, Neher et al., *Scientific American*, vol. 266, pp. 44-51, Mar. 1992.

*A Novel Method for Glass Micropipette Polishing for Electropatch Clamp Recording Using Oxygen Plasma*, Itoh et al., *Biochemical and Biophysical Research Communications*, vol. 191, No. 2, pp. 447-452, 1993.

*Fast 3D Laser Micromachining of Silicon for Micromechanical and Microfluidic Applications*, Mullenborn et al., *The 8th International Conference on Solid-State Sensors and Actuators, and Eurosensors IX*, pp. 166-169, Jun. 25-29, 1995.

*A Practical Guide to Patch Clamping*, Penner, *Single-Channel Recording*, pp. 3-30, 1995.

*Geometric Parameters of Pipettes and Membrane Patches*, Sakmann et al., *Single-Channel Recording*, pp. 637-650, 1995.

*Glass-Funnel Technique for the Recording of Membrane Currents and Intracellular Perfusion of Xenopus Oocytes*, Shuba et al., *Pflugers Arch.—Eur. J. Physiol.*, vol. 432, pp. 562-570, 1996.

*Seal-Promoting Solutions and Pipette Perfusion for Patch Clamping Plant Cells*, Maathuis et al., *The Plant Journal*, vol. 11, No. 4, pp. 891-896, 1997.

*A 0.1-700 Hz Current Through a Voltage-Clamped Pore: Candidate Protein for Initiator of Neural Oscillations*, McGeoch et al., *Brain Research*, vol. 766, pp. 188-194, 1997.

*HTS Approaches to Voltage-Gated Ion Channel Drug Discovery*, Denyer et al., *Drug Discovery Today*, vol. 3, No. 7, pp. 323-332, Jul. 1998.

*Cell-Based Assays and Instrumentation for Screening Ion-Channel Targets*, Gonzalez et al., *Drug Discovery Today*, vol. 4, No. 9, pp. 431-439, Sep. 1999.

*Characterization of a Micromachined Planar Patch Clamp for Cellular Electrophysiology*, Matthews et al., *1st International IEEE EMBS Neural Engineering Conference*, pp. 1-4. Mar. 20-22, 2003.

*Automated Electrophysiology: High Throughput of Art*, Wang et al., *Assay and Drug Development Technologies*, vol. 1, No. 5, pp. 695-708 (reprint pp. 1-13), Oct. 2003.

*High Throughput Ion-Channel Pharmacology: Planar-Array-Based Voltage Clamp*, Kiss et al., *Assay and Drug Development Technologies*, vol. 1, No. 1, Part 2, pp. 127-135, Feb. 2003.

*Patchers v. Screeners: Divergent Opinion on High Throughput Electro-physiology*, Comley, *Drug Discovery World*, pp. 47-57, Fall 2003.

*High Throughput Electrophysiology: New Perspectives for Ion Channel Drug Discovery*, Willumsen, *Receptors and Channels*, vol. 9, No. 1, pp. 3-12, 2003.

*High Throughput Electrophysiology Using a Fully Automated, Multiplexed Recording System*, Trumbull et al., *Receptors and Channels*, vol. 9, No. 1, pp. 19-28, 2003.

*Microstructured Apertures in Planar Glass Substrates for Ion Channel Research*, Fertig et al., *Receptors and Channels*, vol. 9, No. 1, pp. 29-40, 2003.

*Upscaling and Automation of Electrophysiology: Toward High Throughput Screening in Ion Channel Drug Discovery*, Asmild et al., *Receptors and Channels*, vol. 9, No. 1, pp. 49-58, 2003.

*CYTOCENTERING: A Novel Technique Enabling Automated Cell-by-Cell Patch Clamping with the CYTOPATCH™ Chip*, Stett et al., *Receptors and Channels*, vol. 9, No. 1, pp. 59-66, 2003.

*Screening Technologies for Ion Channel Targets in Drug Discovery*, Zheng et al., *American Phamaceutical Review*, pp. 85-92, 2003.

*Planar Patch Clamping not an Automatic Choice*, Shah, *Drug Discovery & Development*, pp. 59-63, Jul. 2004.

*Fabrication of a Novel Microsystem for the Electrical Characterisation of Cell Arrays*, Hediger et al., *Sensors and Actuators*, vol. 56, pp. 175-180, 1999.

*Electroporation of Cells and Tissues*, Weaver, *IEEE Transactions on Plasma Science*, vol. 28, No. 1, pp. 24-33, Feb. 2000.

*Characterization of Single-Cell Electroporation by Using Patch-Clamp and Fluorescence Microscopy*, Ryttsen et al., *Biophysical Journal*, vol. 79, pp. 1993-2001, Oct. 2000.

*Biological-to-Electronic Interface with Pores of ATP Synthase Subunit C in Silicon Nitride Barrier*, McGeoch et al., *Medical & Biological Engineering & Computing*, vol. 38, pp. 113-119, 2000.

*Microstructured Glass Chip for Ion-Channel Electrophysiology*, Fertig et al., *Physical Review E*, vol. 64, No. 4, Part 1, pp. 040901-1 to 040901-4, Sep. 2001.

*Ion-Channel Assay Technologies: Quo Vadis?*, Xu et al., *Drug Discovery Today*, vol. 6, No. 24, pp. 1278-1287, Dec. 2001.

*Whole Cell Patch Clamp Recording Performed on a Planar Glass Chip*, Fertig et al., *Biophysical Journal*, vol. 82, pp. 3056-3062, Jun. 2002.

*Micromolded PDMS Planar Electrode Allows Patch Clamp Electrical Recordings From Cells*, Klemic et al., *Biosensors and Bioelectronics*, vol. 17, pp. 597-604, Jun. 2002.

An Interview with Kirk S. Schroeder, President, Essen Instruments, *Assay and Drug Development Technologies*, vol. 1, No. 1-1, pp. 3-8, 2002.

IonWorks™ HT: A New High-Throughput Electrophysiology Measurement Platform, Schroeder et al., *Journal of Biomolecular Screening*, vol. 8, No. 1, pp. 50-64, Feb. 2003.

Characterization, Toxicity and Therapeutic Efficacy of Adriamycin Encapsulated in Liposomes, Olson et al., *European Journal of Cancer & Clinical Oncology*, vol. 18, No. 2, pp. 167-176, Feb. 1982 (abstract only).

Impedance Analysis of Support Lipid Bilayer Membranes: A Scrutiny of Different Preparation Techniques, Steinem et al., *Biochimica et Biophysica Acta*, vol. 1279, pp. 169-180, 1996.

Planar Lipid Bilayers on Solid Supports From Liposomes—Factors of Importance for Kinetics and Stability, Puu et al., *Biochimica et. Biophysica Acta*, vol. 1327, pp. 149-161, 1997.

Automated Patch-Clamps Enable Faster Ion Screening, McGee, *Drug Discovery & Development*, pp. 51-53, Jan. 2005.

Characterization of a hERG Screen Using the IonWorks HT: Comparison to a hERG Rubidium Efflux Screen, Sorota et al., *Assay and Drug Development Technologies*, vol. 3, No. 1, pp. 47-57, 2005.

*Cloe Screen™ hERG Safety Single Cell Planar Patch Clamp Method* article/information pages, Cyprotex, undated (internet print date May 4, 2005).

\* cited by examiner

SYSTEM FOR RAPID CHEMICAL ACTIVATION IN HIGH-THROUGHPUT ELECTROPHYSIOLOGICAL MEASUREMENTS

REFERENCE TO RELATED APPLICATION

This application is a continuation-in-part of U.S. patent application Ser. No. 09/631,909 filed Aug. 4, 2000, now U.S. Pat. No. 6,488,829, entire contents of which are incorporated herein by reference.

FIELD OF INVENTION

The present invention relates generally to the field of electrophysiology, wherein electrical measurements are made on biological cells and cell membranes to understand interactions between specific membrane components such as ion channels and transporters. More particularly, the invention relates to apparatus and methods for rapidly introducing an activating chemical agent into multiple measurement wells in parallel, thereby enabling the study of fast ligand-gated electrophysiological events in a high-throughput manner.

BACKGROUND OF INVENTION

The electrical behavior of cells and cell membranes is of profound importance in basic research as well as in modem drug development. As described in the above-reference parent applications, a specific area of interest in this field is in the study of ion channels and transporters. Ion channels are protein-based pores found in the cell membrane that are responsible for maintaining the electro-chemical gradients between the extra cellular environment and the cell cytoplasm.

Quite often these membrane channels are selectively permeable to a particular type of ion, e.g. potassium or sodium. The channel is generally comprised of two parts; the pore itself, and a switch mechanism that regulates (gates) the conductance of the pore. Examples of regulation mechanisms include changes in transmembrane voltage or the activation or deactivation of a membrane receptor via a chemical ligand. Ion channels are passive elements in that once opened, ions flow in the direction of existing chemical gradients. Ion transporters are similar in that they are involved in the transport of ions across the cell membrane, however they differ from ion channels in that energy is required for their function and they tend to actively pump against established electrochemical gradients.

An interesting and technically challenging aspect of ion channels involves their rapid and quite diverse signaling kinetics. Many ion channels can be activated and then de-activated in a few milliseconds. This requires that the instrumentation used in their analysis have the ability to following these changes with a fairly high temporal bandwidth, on the order of 10 kHz.

For an instrument to resolve these kinds of changes it is not only necessary that the recording apparatus have the required temporal bandwidth, but in addition the method of stimulating the ion channel event must also be fast. The electrical recording aspect of this problem is involved but readily achievable since high-bandwidth operational amplifiers are readily available.

The issue of achieving a rapid stimulus deserves additional explanation. As previously mentioned, some ion channels are activated by voltage. In these cases the same electronics used to record ion channel currents can also be used to control the voltage stimulus. This type of measurement is common in the industry and is referred to as a voltage clamp. In this case the time bandwidth of the stimulus, an electrical signal, is inherently fast enough so as not to degrade the kinetics of the voltage-gated ion channel signals.

Another class of ion channel events relies on chemical or "ligand" gating. These kinetic channel events are activated by specific chemical messengers such as the release of intracellular calcium, adenosine 3',5'—monophosphate (cyclic AMP or cAMP) or acetylcholine (ACh). It is beyond the scope of this application to discuss all of the potential signaling chemicals that are of biological or therapeutic interest and the above serve only as examples. It should be mentioned, however, that in some cases the chemical activation of an ion channel is extra-cellular in its initiation, and in other cases it is intra-cellular. This implies that not only is it important that the compound can be released on the time scale of tens of milliseconds, but in some cases it is desirable to have it introduced within the membrane of a living cell.

One technique for accomplishing rapid stimulation of ligand-gated channels utilizes photo-activatable or "caged" compounds. This term refers to chemicals which are chemically altered such that the active nature of the compound is suppressed ("caged") until photo-activated, usually by a short pulse of ultra-violet (UV) light of wavelength in the range of 240 and 400 nm.

The photolysis of such compounds is very fast and thereby can rapidly (in some cases in microseconds) release the active species of the compound. The underlying chemistry for making various common biological chemicals photoa-activatable is well-developed and the "caged" version of many compounds are commercially available for purchase through companies such as Molecular Probes of Eugene, Oreg.. In addition, when intracellular application is required, the caged version can often be made cell permeable such that it can be loaded into the cytoplasm of the cell for rapid intra-cellular activation at a later time The technique of using pulsed UV illumination of a biological sample to rapidly release chemicals is fairly common in the fields of rapid cellular imaging and single-well patch-clamp electrophysiology. Parpura describes a system that utilizes a micro-manipulated optical fiber to deliver UV energy for flash photolysis in support of microscopic imaging studies. U.S. Pat. No. 5,936,728, describes a flash photolysis system for use in a scanning microscope allowing for automatic alignment of the ultraviolet directed beam and the detected image point in time. To date, there has been no utilization of this technique in the field of high-throughput (i.e., non-patch clamp) electrophysiology as described in the parent to this application.

SUMMARY OF THE INVENTION

This invention improves upon, and extends, the teachings of U.S. Pat. No. 6,488,829, which resides in high-throughput electrophysiological measurements. This integrated electrophysiogical measurement system includes a computer-controlled data collection system, an integrated electronics head for making parallel electrical measurements, and an integrated fluidics head used in part to transfer test compounds into the measurement process.

To this basic configuration, the instant invention introduces additional components facilitating computer control of a pulsed ultra-violet (UV) light source. This light source, and associated light coupling to a plurality of test samples, is used in conjunction with the other instrumentation to make effectuate high-throughput electrical measurements with respect to fast-acting, chemically-activated electrophysiological events.

DETAILED DESCRIPTION OF THE INVENTION

In contrast to prior-art patch clamp techniques, wherein a glass pipette is used to form a high-resistance electrical seal with a single biological membrane, commonly assigned U.S. Pat. No. 6,488,829 describes a technique wherein a plurality of minute apertures in a two-dimensional substrate provide the requisite sealing function. The advantage of this approach is that it eliminates the need for micromanipulation of an electrode assembly by a skilled user, while providing a format suitable for achieving multiple electrical seals in parallel, dramatically increasing the measurement throughput of the device.

Figure 1:
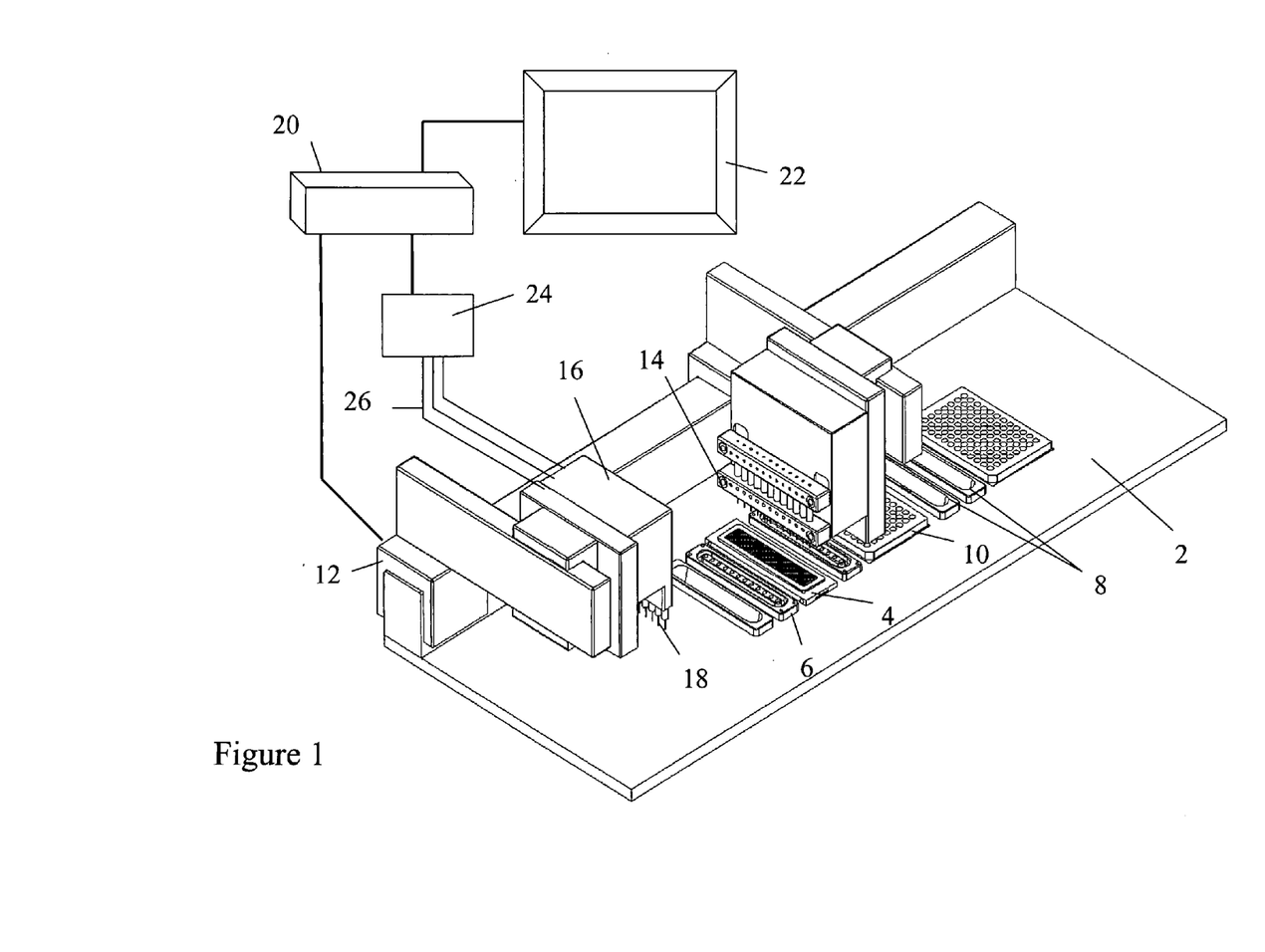
FIG. 1 is a drawing which shows a high-throughput screening system according to the invention including a UV illumination module and integrated fluidics head for parallel operations.

To review, a specific embodiment of the system architecture enabling electrophysiological measurements to be conducted simultaneously on a plurality of cells (e.g. an N×M grid) is shown in FIG. 1. This architecture is comprised of several subsystems including a measurement platform (2) containing positions for a multi-well electrophysiogical measurement substrate (4), wash stations (6), reagent stations (8) and trays for containing potential drug candidates (10).

Included with this measurement platform is a 3-D mechanical gantry system (12) capable of independently moving a multi- or single-channel fluidics head (14) and electronics read head (16). The fluidics head and the electronics head could, without loss of function, both be comprised of single probes, N×1 (1-dimensional) as shown here or N×M (2-dimensional) geometries. The gantry system allows for the transfer of potential drug candidates to the various N×M "wells" of the multi-well measurement substrate using the fluidics head (14) as well as for spatially selectable electrical recording via a plurality of electrodes (18). Also shown is a data storage and processing unit (20) and user interface CRT display (22).

The present invention includes a UV light source module (24) which is capable of coupling light through a light coupler (26) into the measurement substrate (4) concurrently with the ability to electronically record currents from the same wells. This adaptation allows for the rapid and direct activation (through UV flash photolysis of a caged compound) and simultaneous electrical recording of time critical, ligand-activated ion channel or ion transporter events.

Figure 2:
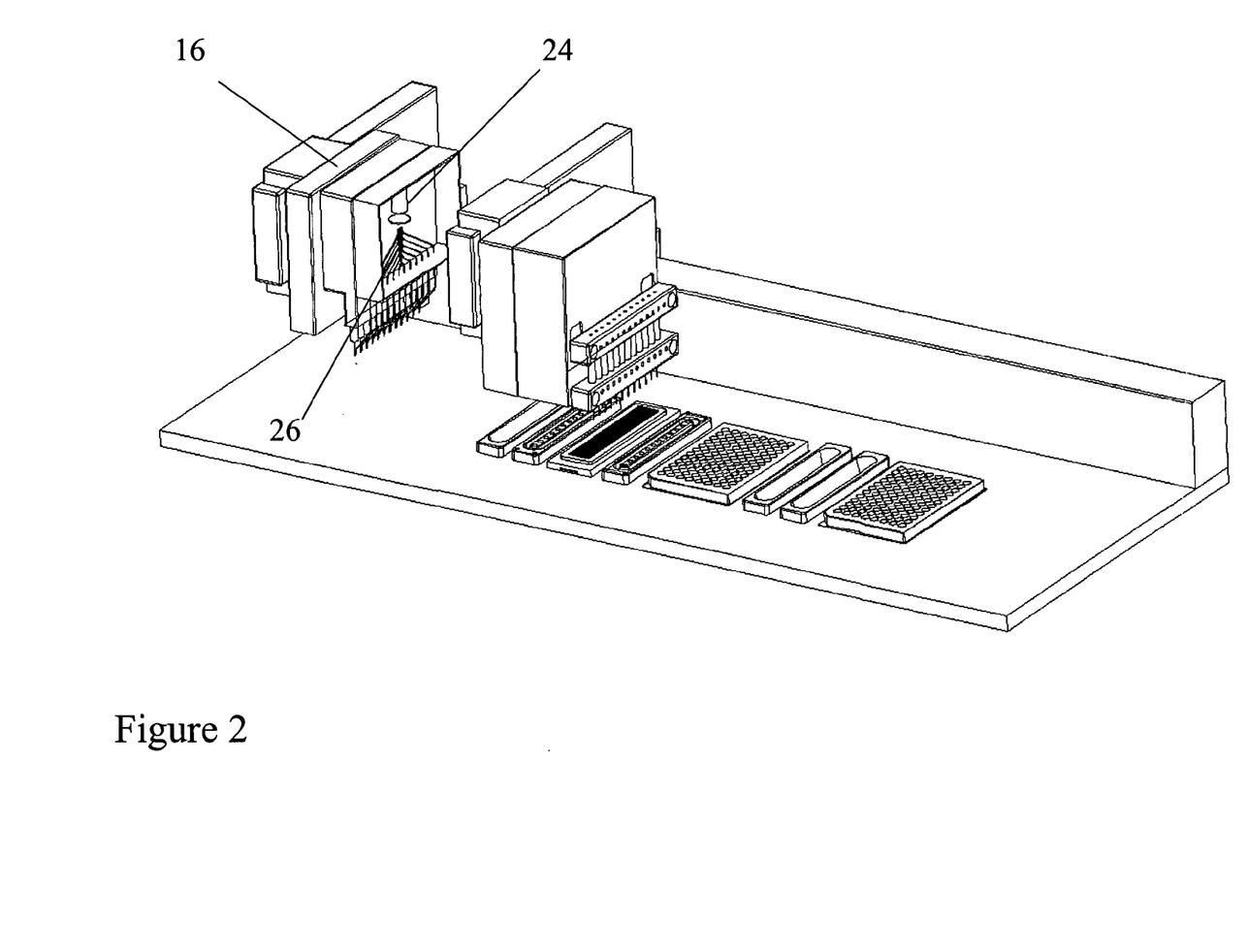
FIG. 2 depicts a preferred embodiment of a UV illumination technique whereby the light energy is directed via optical fibers to the biological samples.

FIG. 2 illustrates one specific embodiment of this invention, whereby a UV light source (24) is controlled by the central processing unit (20). CPU (20) is preferably capable of controlling the optical pulsewidth and intensity of the source such that the timing, duration and light energy of the ultraviolet exposure can be automatically controlled. The light is preferably fed via optical fibers (26) to the sample through the electronic read head assembly (16). As a further alternative, the light may be coupled to the biological sample by other means, for example, by free space optics or evanescent wave coupling through the base of the substrate. Conventional optical elements such as mirrors, beam splitters, diffusers, collimators, telescopic optics, and the like may also be used as appropriate in place of, or in addition to the components previously described.

I claim:

1. An electrophysiological measurement apparatus for analyzing a biological material, comprising:
   a multi-well plate having a plurality of fluid chambers, wherein each fluid chamber is configured to hold a biological material to be analyzed;
   a thin plastic substrate having an array of apertures in alignment with the chambers of the multi-well plate;
      wherein the substrate is bonded to the multi-well plate such that the chambers are open at the top and sealed at the bottom, except for the apertures;
      wherein the apertures are smaller in diameter than the biological material, thereby enabling a high-resistance seal to be formed between a biological material present in each chamber and a corresponding aperture; and
      wherein the substrate has a glass coating at least in the region where the high-resistance seal is formed between the biological material and the substrate; a fluid plenum to receive the multi-well plate such that at least the substrate is immersed;
   a first electrode disposed in the fluid plenum;
   at least one second electrode adapted to fit into the top openings of the fluid chambers of the multi-well plate;
   a light source for illuminating one or more of the chambers so as to facilitate the rapid release of a caged compound present therein; and
   electrophysiological measurement circuitry in electrical communication with the electrodes.

2. The electrophysiological measurement apparatus of claim 1, wherein the light source is an ultraviolet light source.

3. The electrophysiological measurement apparatus of claim 1, wherein a single aperture is associated with each chamber of the multi-well plate.

4. The electrophysiological measurement apparatus of claim 1, wherein the substrate includes mylar or polyimide.

5. The electrophysiological measurement apparatus of claim 1, wherein the diameters of the apertures are in the range of 1 to 10 micrometers.

6. The electrophysiological measurement apparatus of claim 1, wherein the apertures are tapered.

7. The electrophysiological measurement apparatus of claim 1, wherein the multi-well plate is sealed to the fluid plenum, enabling a differential pressure to be applied relative to the fluid in each chamber, thereby causing the material in each chamber to migrate to a respective aperture.

8. The electrophysiological measurement apparatus of claim 1, wherein the fluid plenum includes a chemical reagent causing a biological material in each chamber to permeabilize in the vicinity of the aperture.

9. The electrophysiological measurement apparatus of claim 1, further comprising a mechanism for moving the at least one second electrode into the chambers of the multi-well plate, so as to automate the measurement of the material contained therein.

10. The electrophysiological measurement apparatus of claim 1, further comprising:
   a plurality of second electrodes in alignment with a plurality of the chambers of the multi-well plate; and a mechanism for moving the plurality of second electrodes into the chambers of the multi-well plate to perform simultaneous measurements on the material contained therein.

11. The electrophysiological measurement apparatus of claim 1, further comprising a system for transferring fluids from one or more sources to the chambers of the multi-well plate.

12. The electrophysiological measurement apparatus of claim 1, further comprising a mechanism for directing the light from the source to the multi-well plate in an automated and spatially selectable manner.

13. The electrophysiological measurement apparatus of claim 1, further comprising a mechanism for directing the light from the source to spatially selected wells in conjunction with a plurality of electrodes, thereby providing for the simultaneous electrical recording of the biological materials during and subsequent to illumination of the materials.

14. The electrophysiological measurement apparatus of claim 1, further comprising an electronic control of optical pulse width and intensity, such that the timing, duration, and energy of the light directed from the light source onto the chambers can be automatically controlled.

15. The electrophysiological measurement apparatus of claim 1, further comprising a guide for coupling the light from the light source directly into the biological materials.

16. The electrophysiological measurement apparatus of claim 15, wherein the guide includes one or more optical fibers.

17. The electrophysiological measurement apparatus of claim 16, wherein the guide includes at least one optical component selected from the group consisting of mirrors, beam splitters, diffusers, collimators, and telescopic optics.

18. The electrophysiological measurement apparatus of claim 1, further comprising at least one of a cell, organelle, and vesicle positioned in at least one of the fluid chambers.

19. The electrophysiological measurement apparatus of claim 1, wherein the system is adapted to measure at least one of an electrical potential difference and a current across at least a portion of a biological material sealed across at least one of the apertures.

20. An electrophysiological measurement apparatus for analyzing a biological material, comprising:
a multi-well plate having a plurality of fluid chambers, wherein each fluid chamber is configured to hold a biological material to be analyzed;
a thin substrate having an array of apertures in alignment with the chambers of the multi-well plate;
  wherein the substrate is bonded to the multi-well plate such that the chambers are open at the top and sealed at the bottom, except for the apertures; and
  wherein the apertures are smaller in diameter than the biological material, thereby enabling a high-resistance seal to be formed between a biological material present in each chamber and a corresponding aperture;
a fluid plenum to receive the multi-well plate such that at least the substrate is immersed;
a first electrode disposed in the fluid plenum;
at least one second electrode adapted to fit into the top openings of the fluid chambers of the multi-well plate;
a light source for illuminating one or more of the chambers so as to facilitate the rapid release of a caged compound present therein;
electrophysiological measurement circuitry in electrical communication with the electrodes; and
a mechanism for moving the at least one second electrode into the chambers of the multi-well plate, so as to automate the measurement of the material contained therein.

21. The electrophysiological measurement apparatus of claim 20, further comprising:
a plurality of second electrodes in alignment with a plurality of the chambers of the multi-well plate; and
a mechanism for moving the plurality of second electrodes into the chambers of the multi-well plate to perform simultaneous measurements on the material contained therein.

22. The electrophysiological measurement apparatus of claim 20, wherein the light source is an ultraviolet light source.

23. The electrophysiological measurement apparatus of claim 20, wherein a single aperture is associated with each chamber of the multi-well plate.

24. The electrophysiological measurement apparatus of claim 20, wherein the substrate includes mylar or polyimide.

25. The electrophysiological measurement apparatus of claim 20, wherein the diameters of the apertures are in the range of 1 to 10 micrometers.

26. The electrophysiological measurement apparatus of claim 20, wherein the apertures are tapered.

27. The electrophysiological measurement apparatus of claim 20, wherein the multi-well plate is sealed to the fluid plenum, enabling a differential pressure to be applied relative to the fluid in each chamber, thereby causing the material in each chamber to migrate to a respective aperture.

28. The electrophysiological measurement apparatus of claim 20, wherein the fluid plenum includes a chemical reagent causing a biological material in each chamber to permeabilize in the vicinity of the aperture.

29. The electrophysiological measurement apparatus of claim 20, further comprising a system for transferring fluids from one or more sources to the chambers of the multi-well plate.

30. The electrophysiological measurement apparatus of claim 20, further comprising a mechanism for directing the light from the source to the multi-well plate in an automated and spatially selectable manner.

31. The electrophysiological measurement apparatus of claim 20, further comprising a mechanism for directing the light from the source to spatially selected wells in conjunction with a plurality of electrodes, thereby providing for the simultaneous electrical recording of the biological materials during and subsequent to illumination of the materials.

32. The electrophysiological measurement apparatus of claim 20, further comprising an electronic control of optical pulse width and intensity, such that the timing, duration, and energy of the light directed from the light source onto the chambers can be automatically controlled.

33. The electrophysiological measurement apparatus of claim 20, further comprising a guide for coupling the light from the light source directly into the biological materials.

34. The electrophysiological measurement apparatus of claim 33, wherein the guide includes one or more optical fibers.

35. The electrophysiological measurement apparatus of claim 34, wherein the guide includes at least one optical component selected from the group consisting of mirrors, beam splitters, diffusers, collimators, and telescopic optics.

36. The electrophysiological measurement apparatus of claim 20, further comprising at least one of a cell, organelle, and vesicle positioned in at least one of the fluid chambers.

37. The electrophysiological measurement apparatus of claim 20, wherein the system is adapted to measure at least one of an electrical potential difference and a current across at least a portion of a biological material sealed across at least one of the apertures.

38. An electrophysiological measurement apparatus, comprising:
- a first fluid chamber, configured to contain a cell or membrane to be measured;
- a second fluid chamber;
- a thin plastic substrate separating the two chambers, the substrate having an aperture formed therethrough which is smaller in diameter than the cell or membrane, thereby enabling a high-resistance seal to be formed between the cell or membrane and the substrate, the substrate further having a glass coating at least in the region where the high-resistance seal is formed between the biological material and the substrate;
- a light source for illuminating one or more of the chambers so as to facilitate the rapid release of a caged compound present therein;
- an electrode disposed in each of the fluid chambers; and
- electrophysiological measurement circuitry in electrical communication with the electrodes.

39. An electrophysiological measurement apparatus, comprising:
- a first fluid chamber, configured to contain a cell or membrane to be measured;
- a second fluid chamber;
- a thin substrate separating the two chambers, the substrate having an aperture formed therethrough which is smaller in diameter than the cell or membrane, thereby enabling a high-resistance seal to be formed between the cell or membrane and the substrate;
- a light source for illuminating one or more of the chambers so as to facilitate the rapid release of a caged compound present therein;
- an electrode disposed in each of the fluid chambers;
- electrophysiological measurement circuitry in electrical communication with the electrodes; and
- a mechanism for moving at least one of the electrodes into a corresponding at least one of the fluid chambers, so as to automate the measurement of the material contained therein.

40. The electrophysiological measurement apparatus of claim 39, further comprising:
- a plurality of first chambers, each configured to contain a cell or membrane to be measured, forming a multi-well plate, wherein the substrate has a plurality of apertures, and wherein the apertures are in alignment with the plurality of first chambers;
- wherein the substrate has a plurality of apertures, in alignment with the plurality of first chambers; and
- wherein the mechanism for moving at least one of the electrodes moves the electrodes into contact with the first chambers.

\* \* \* \* \*